(12) United States Patent
Meyer et al.

(10) Patent No.: US 6,651,483 B1
(45) Date of Patent: Nov. 25, 2003

(54) LOW LEAK GAS DENSITY MONITOR ASSEMBLY

(75) Inventors: Jeffry R. Meyer, Greensburg, PA (US); Willie B. Freeman, Irwin, PA (US); Caroline Komlenic, Pittsburgh, PA (US)

(73) Assignee: ABB Technology AG, Zurich (CH)

(*) Notice: Subject to any disclaimer, the term of this patent is extended or adjusted under 35 U.S.C. 154(b) by 53 days.

(21) Appl. No.: 09/946,235

(22) Filed: Sep. 5, 2001

(51) Int. Cl.$^7$ ........................... F16K 37/00; F16L 55/02; F16L 17/02; F16L 27/00; G01N 31/00
(52) U.S. Cl. .................. 73/23.28; 73/31.05; 137/382; 137/552; 137/614.06
(58) Field of Search .................. 73/23.28, 23.2, 73/31.05; 137/614.05–614.06, 552, 586, 382

(56) References Cited

U.S. PATENT DOCUMENTS

| | | | |
|---|---|---|---|
| 3,063,287 A | 11/1962 | Hubbard | 73/30 |
| 3,365,932 A | 1/1968 | Greene, Jr. | 73/30 |
| 3,427,862 A * | 2/1969 | Hubner | 73/23.2 |
| 3,933,029 A * | 1/1976 | Rabenecker et al. | 73/23.2 |
| 4,106,350 A | 8/1978 | Morris et al. | 73/755 |
| 4,279,142 A | 7/1981 | McIntyre | 73/1 G |
| 4,476,706 A | 10/1984 | Hadden et al. | 73/1 G |
| 4,485,845 A | 12/1984 | Brady | 137/614.04 |
| 4,590,789 A | 5/1986 | Kunze | 73/1 G |
| 4,736,617 A * | 4/1988 | Huhmer et al. | 73/23.2 |
| 4,871,195 A | 10/1989 | Parrish | 285/91 |
| 4,889,368 A | 12/1989 | Laipply | 285/18 |
| 5,143,114 A | 9/1992 | Daniels | 137/385 |
| 5,177,468 A | 1/1993 | Baldwin et al. | 340/652 |
| 5,248,168 A | 9/1993 | Chichester et al. | 285/49 |
| 5,377,528 A * | 1/1995 | Dauvergne | 73/31.01 |
| 5,388,451 A | 2/1995 | Stendin et al. | 73/438 |
| 5,404,923 A * | 4/1995 | Yamamoto et al. | 141/279 |
| 5,417,204 A * | 5/1995 | Moesle, Jr. | 128/205.23 |
| 5,520,207 A | 5/1996 | Newsome et al. | 137/15 |
| 5,582,797 A * | 12/1996 | Kewley et al. | 422/83 |
| 5,629,471 A | 5/1997 | King | 73/1.01 |
| 5,665,894 A | 9/1997 | Baker | 73/1.05 |
| 5,679,535 A * | 10/1997 | Joyce et al. | 435/7.9 |
| 5,693,873 A | 12/1997 | Thuries et al. | 73/23.28 |
| 5,733,506 A * | 3/1998 | Silver et al. | 422/90 |
| 5,789,660 A * | 8/1998 | Kofoed et al. | 73/23.2 |
| 5,969,223 A * | 10/1999 | Nagai et al. | 73/1.06 |
| 6,263,914 B1 | 7/2001 | Meyer et al. | 137/552 |
| 6,418,783 B2 * | 7/2002 | Sunshine et al. | 73/29.01 |

* cited by examiner

Primary Examiner—Helen Kwok
Assistant Examiner—David J. Wiggins
(74) Attorney, Agent, or Firm—Woodcock Washburn LLP

(57) ABSTRACT

An apparatus is provided for monitoring the fluidic contents of a tank. The tank includes a quick disconnect valve and an assembly includes a monitor device, such as, for example, a gas density monitor, a pressure monitor, a temperature monitor, etc., and a quick disconnect fitting. The monitor device is coupled to the quick disconnect fitting. The quick disconnect fitting is adapted to couple to the quick disconnect valve such that the interior of the quick disconnect fitting is in fluidic communication with the interior of the monitor device for reducing the chance of leakage upon connection/disconnection.

27 Claims, 10 Drawing Sheets

Section C-C

LOW LEAK GAS DENSITY MONITOR ASSEMBLY

FIELD OF THE INVENTION

The present invention relates generally to gas monitors for an enclosure. More particularly, the present invention relates to an assembly for attaching, with a quick disconnect coupling, a gas density monitor to an enclosure containing, for example, electrical switch gear.

BACKGROUND OF THE PRESENT INVENTION

In many electrical power components, a switch is used to control current flow through a conductor. Opening a current-carrying conductor may cause arcing, which may be harmful to the switch. To minimize arcing, such a switch is typically contained in an enclosure (e.g., a tank) and the enclosure is typically filled with an insulating gas. The gas minimizes arcing upon opening or closing a current carrying conductor.

In order to ensure that the gas will perform its insulating task as designed, it is important that the gas within the tank is maintained within a pre-selected density range. Since tanks may leak over time, allowing gas to escape from the tank, the density of the gas is usually constantly monitored by a gas monitoring system.

FIGS. 1A and 1B illustrate a prior art gas monitoring system. As illustrated in those Figures, a network of pipes 2 feeds the gas from each of the three tanks 3 back to a single density monitor device. As one might expect, if the density falls to an insufficient level, this design makes it difficult to determine the location (i.e., which tank is actually experiencing the leak) and exposes all of the circuit breakers to failure from a leak in a single tank. Moreover, the intricate piping network also creates more places for leaks to occur (e.g., at threaded connections in the network of pipes).

To overcome such a problem, a monitoring system may include one density monitor device coupled to each of the three tanks 3. In this manner, each tank is separately monitored and the need for some of the intricate piping is avoided. However, such a system typically includes traditional gas piping having threaded connections and this traditional gas piping is a source of much gas leakage.

One system of minimizing the amount of traditional gas piping is described in U.S. patent application Ser. No. 09/288,678 filed Apr. 9, 1999, entitled "Gas Density Monitor Assembly". The system includes a valve that couples the tank to the gas density monitor. The system considerably reduces the amount of traditional gas piping by mounting the gas density monitor, via the valve, to the tank. Since the gas density monitor is mounted proximate to the tank, the amount of piping required is significantly reduced, thereby minimizing the chance for leakage. In addition, in one embodiment, the valve has a handle and the gas density monitor has a cover. The valve handle is configured such that when the monitor and cover are coupled to the valve, the valve is open. Also, the valve handle is configured to prevent the cover from being placed back on the gas density monitor when the valve is closed. In this manner, the system insures that a valve that was shut-off during testing is not inadvertently left shut-off when testing is complete. This system is a significant improvement over the previous art and provides reduced leakage and a way to insure that the valve is reopened after testing. However, the valve may inadvertently be left open during testing. If the valve is left open during testing, gas may escape from the tank.

Thus, there is a need for a low leak gas density monitoring apparatus that provides a fail-safe connection.

SUMMARY OF THE PRESENT INVENTION

The present invention meets the above need for a fail-safe low leak gas density monitor by providing an assembly for monitoring the fluidic contents of a tank having a quick disconnect valve.

According to an aspect of the present invention, the assembly includes a monitor device, a quick disconnect fitting, and a monitor cover. The monitor device is coupled to the quick disconnect fitting such that fluidic pressure may pass through the quick disconnect fitting to the monitor device. That is, the quick disconnect fitting is coupled to the monitor device such that interior of the quick disconnect fitting is in fluidic communication with the interior of the monitor device. The quick disconnect fitting is adapted to be coupled to the quick disconnect valve of the tank, thereby allowing the fluidic contents of the tank to be in fluidic communication with the density monitor. The monitor cover is coupled to the monitor device, such that, when the quick disconnect fitting is coupled to the quick disconnect valve, the monitor cover is coupled to the tank.

The quick disconnect valve is closed when there is no corresponding quick disconnect fitting coupled to it. The quick disconnect valve is open when there is a corresponding quick disconnect fitting coupled to it. In this manner, the quick disconnect valve is always in the proper state and is therefore, fail-safe. That is, the valve automatically closes upon removal of the quick disconnect fitting and automatically opens upon coupling of the quick disconnect fitting. This provides a fail-safe valve, as well as provides little gas loss upon removal of the quick disconnect fitting.

According to another aspect of the present invention the quick disconnect valve is coupled to the tank with a double o-ring seal and the quick disconnect fitting is coupled to the quick disconnect valve with a double o-ring seal. The double o-ring seals provide a reliable robust sealing system, even if mounting bolts are not fully tightened.

According to a further aspect of the present invention, the monitor device cover is disposed over the monitor device and against the outside wall of the tank to maintain the monitor device at approximately the temperature of the tank, theoretically providing a more accurate estimation of gas density. In one embodiment of the invention, the monitor cover is coupled to the outside wall of the tank via a gasket.

Other features and advantages of the present invention are disclosed below.

DETAILED DESCRIPTION OF ILLUSTRATIVE EMBODIMENTS

The present invention is directed to monitoring the fluidic contents of a tank with a monitor device coupled to the tank via a quick disconnect valve and fitting such that the interior of the tank is in fluidic communication with the interior of the monitor device.

One application for the present invention is in tanks or vessels containing high voltage circuit breakers. Therefore, a portion of this section includes a description of such devices; however, it is contemplated that the present invention may be applied to other enclosures. For example, the present invention may be employed in association with a circuit switcher enclosure, a circuit breaker enclosure, a load break switch enclosure, a recloser enclosure, a storage tank, a reactor, and the like.

A high voltage circuit breaker is a device used in the transmission and distribution of electrical energy. When a sensor or protective relay detects a fault or other system disturbance on the protected circuit, the circuit breaker operates to physically separate current-carrying contacts in each of the three phases by opening the circuit to prevent the continued flow of current. In addition to its primary function of fault current interruption, a circuit breaker is capable of load current switching. A circuit switcher and a load break switch are other types of switching devices.

The major components of a circuit breaker or recloser include interrupters, which function to open and close one or more sets of current carrying contacts housed therein; an operating mechanism, which provides the energy necessary to open or close the contacts; an arcing control mechanism and interrupting media, which interrupt current and create an open condition in the protected circuit; one or more tanks for housing the interrupters; and bushings, which carry electrical energy from the protected circuit into and out of the tank(s). In addition, a mechanical linkage connects the interrupters and the operating mechanism.

Circuit breakers can differ in overall configuration. However, the operation of most circuit breakers is substantially the same. For example, a circuit breaker may include a single tank assembly which houses all of the interrupters. Alternatively, a separate tank for each interrupter may be provided in a multiple tank configuration. An example of such a multiple tank circuit breaker is depicted in FIGS. 1A and 1B.

Figure 1A:
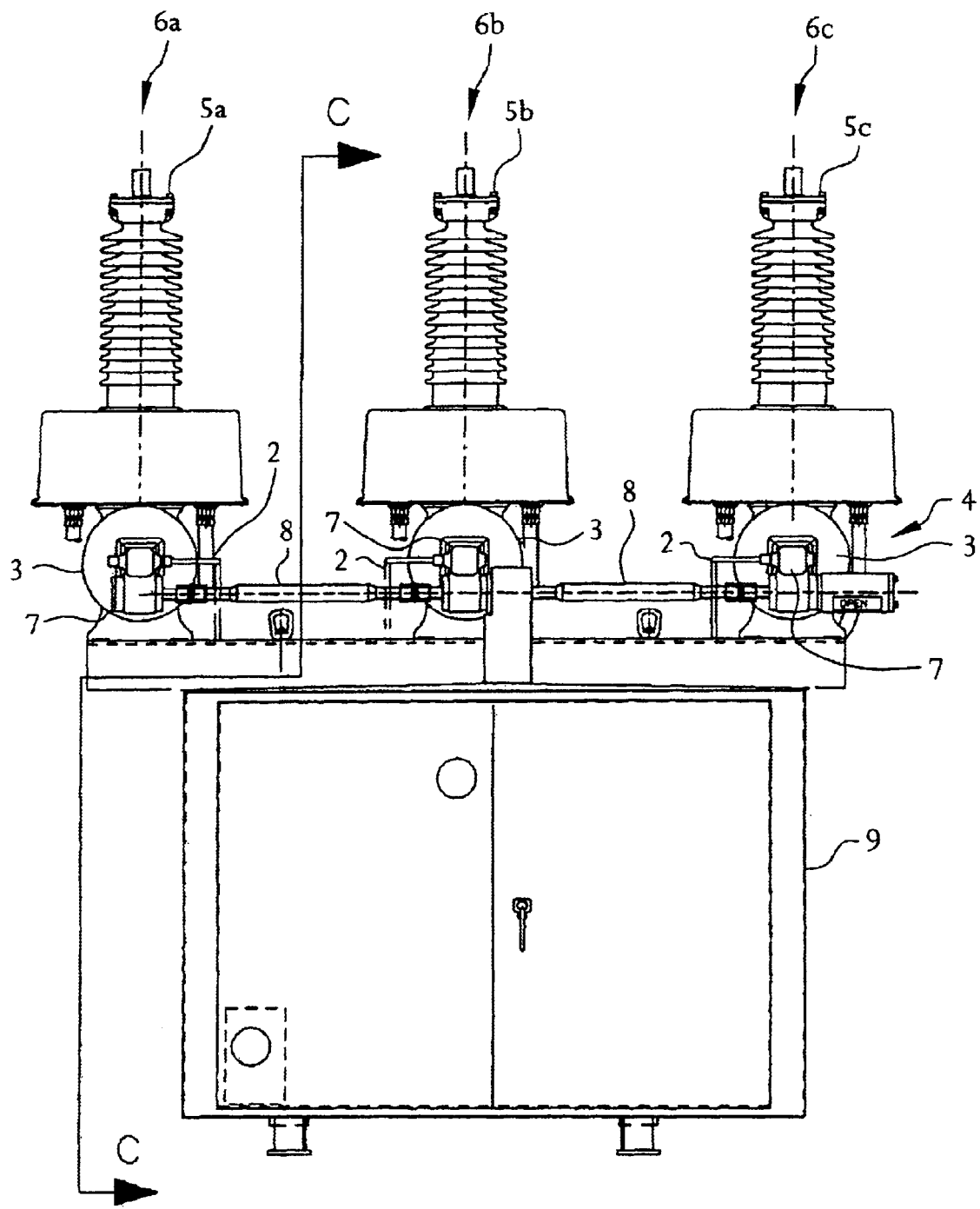
FIG. 1A is a front plan view of an exemplary multiple tank high voltage circuit breaker with which the present invention may be employed.
Figure 1B:
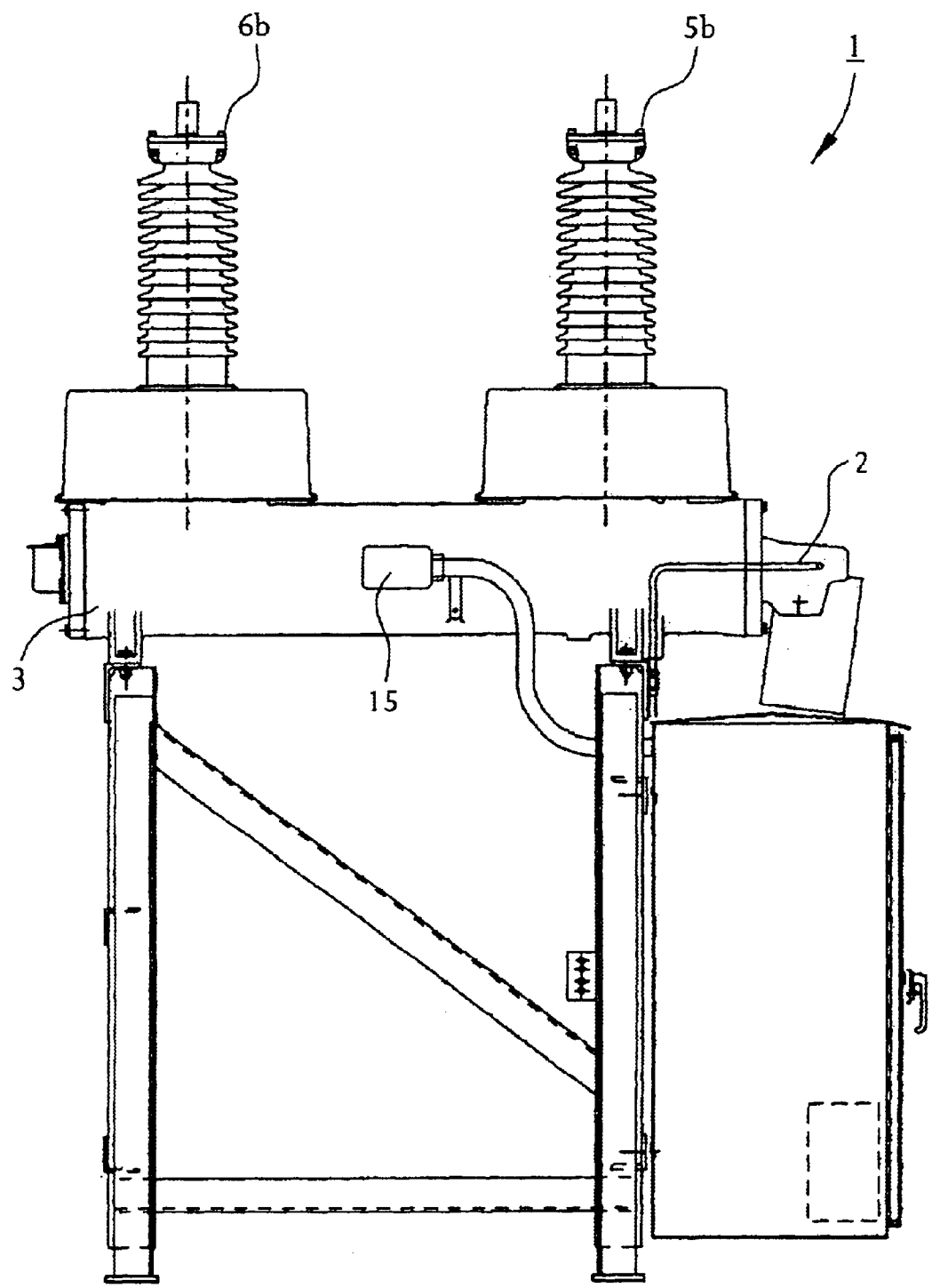
FIG. 1B is a side view of the multiple tank high voltage circuit breaker of FIG. 1A taken along line C—C of FIG. 1A.

As shown in FIGS. 1A and 1B, circuit breaker assembly 1 includes three cylindrical tanks 3. The three cylindrical tanks 3 form a common tank assembly 4 which is preferably filled with an inert, electrically insulating gas such as $SF_6$. The tank assembly 4 is referred to as a "dead tank" because it is at ground potential. Each tank 3 houses an interrupter (not shown). The interrupters are provided with terminals which are connected to respective spaced bushing insulators. The bushing insulators are shown as bushing insulators 5a and 6a for the first phase; 5b and 6b for the second phase; and 5c and 6c for the third phase. Associated with each pole or phase is a current transformer 7. The operating mechanism that provides the necessary operating forces for opening and closing the interrupter contacts is contained within an operating mechanism housing 9. The operating mechanism is mechanically coupled to each of the interrupters via a linkage 8.

During circuit breaker opening or closing, a high voltage potential develops across the contacts. As a result, an electrical arc can develop across the switch contacts, particularly the closer the contacts are to closure. It is desirable to minimize this arc. For this and other reasons, such circuit breakers are typically housed in tanks 3 which are then filled with an inert gas such as $SF_6$, which acts as an insulator to minimize arcing.

In order to ensure that the gas will perform its insulating task as designed, it is important that the gas within the tank is maintained within a preselected density range. Since tanks may leak over time, allowing the inert gas to escape from the tank, the density of the gas is usually constantly monitored.

Many other enclosures, in addition to electrical breaker and switch tanks, use gas density monitoring. For example, some storage tanks that are purged use gas density monitoring. The storage tank contains a liquid and the air space above the liquid, but within the tank, is purged with a gas to displace oxygen. The tank may be purged to reduce the chance of fire or for some other processing reason. The present invention may also be applied to such tanks.

Figure 2:
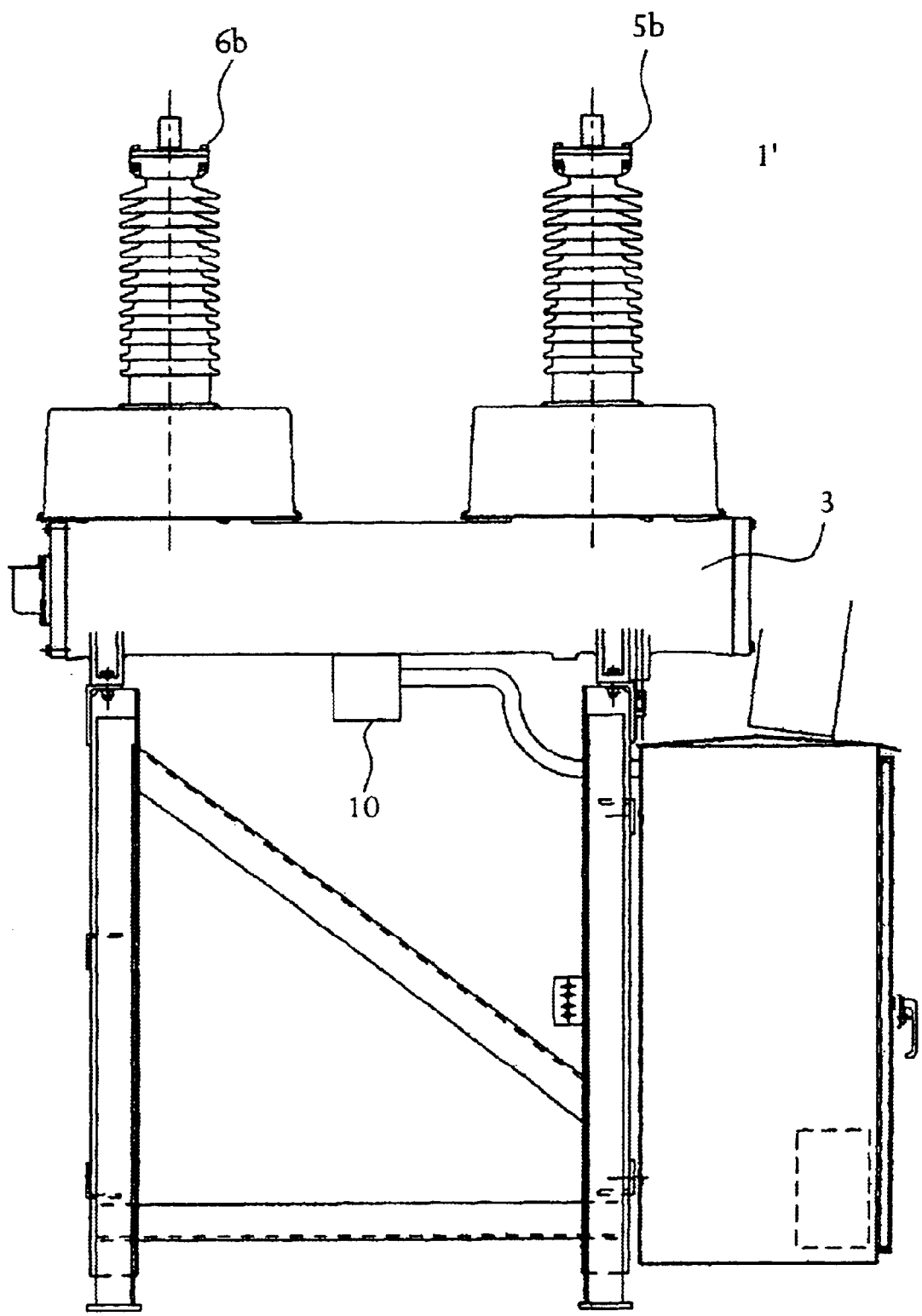
FIG. 2 is a side view of a multiple tank high voltage circuit breaker incorporating a gas density monitoring assembly in accordance with one embodiment of the present invention.

Referring again to an electrical enclosure, FIG. 2 illustrates a circuit breaker assembly employing one embodiment of the present invention. As shown therein, a circuit breaker assembly 1' includes three cylindrical tanks 3 (only one tank is visible in the drawing).

A density monitoring apparatus 10 is coupled to each tank 3. Density monitoring apparatus 10 measures the density of the inert gas directly at the tank and sends an electronic signal indicative of density or discrete density levels. back to a control panel (not shown). Because each density monitoring apparatus 10 measures a tank's gas density directly, the network of gas carrying pipes is eliminated. Also, each tank can be separately monitored for low gas density levels. Importantly, each density monitoring apparatus 10 is coupled to its corresponding tank 3 with a quick disconnect fitting, as described in more detail below.

Figure 3:
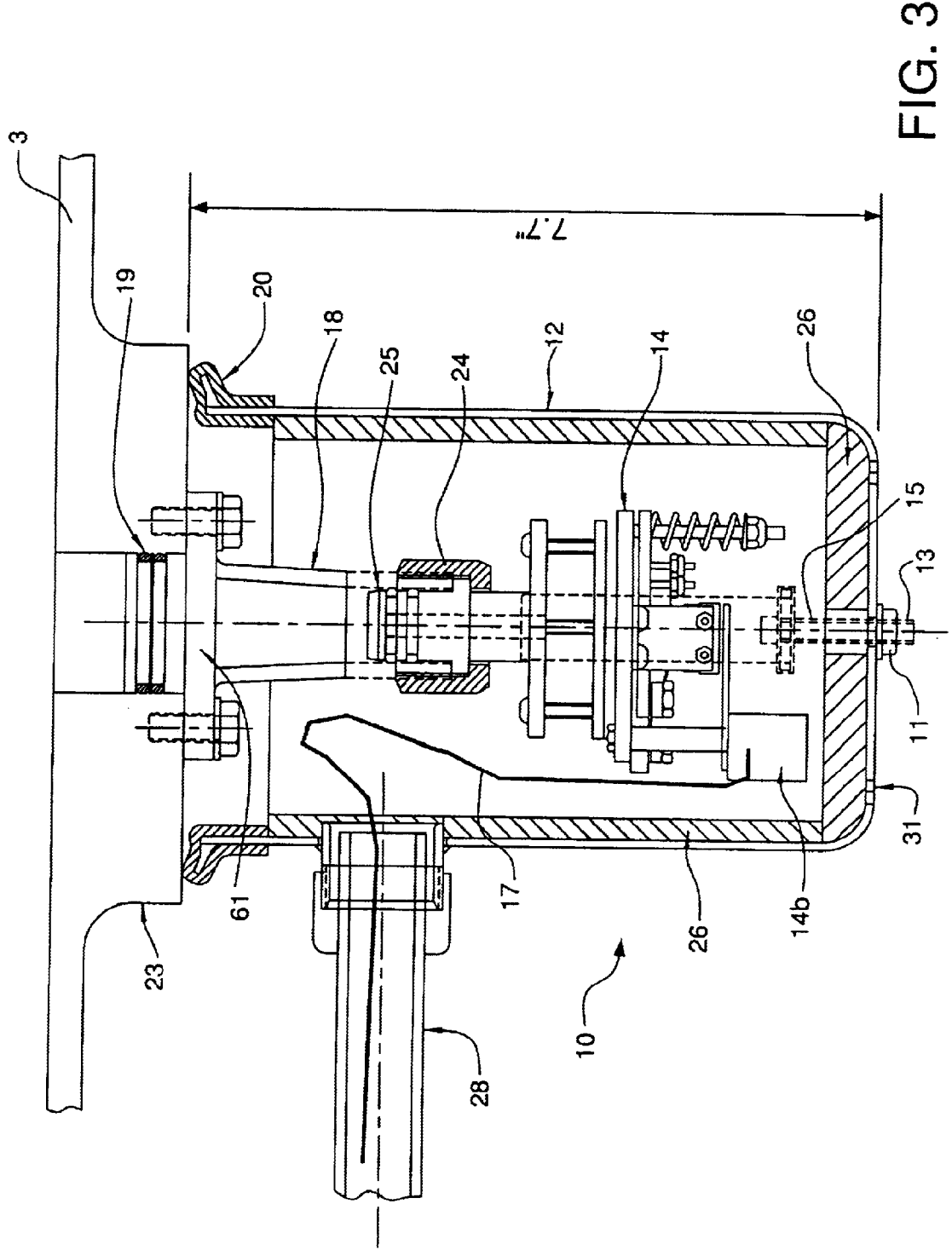
FIG. 3 is a cut-away side view of the gas density monitoring assembly of FIG. 2 connected to a tank that illustrates the interior components of the assembly, in accordance with one embodiment of the present invention.
Figure 4:
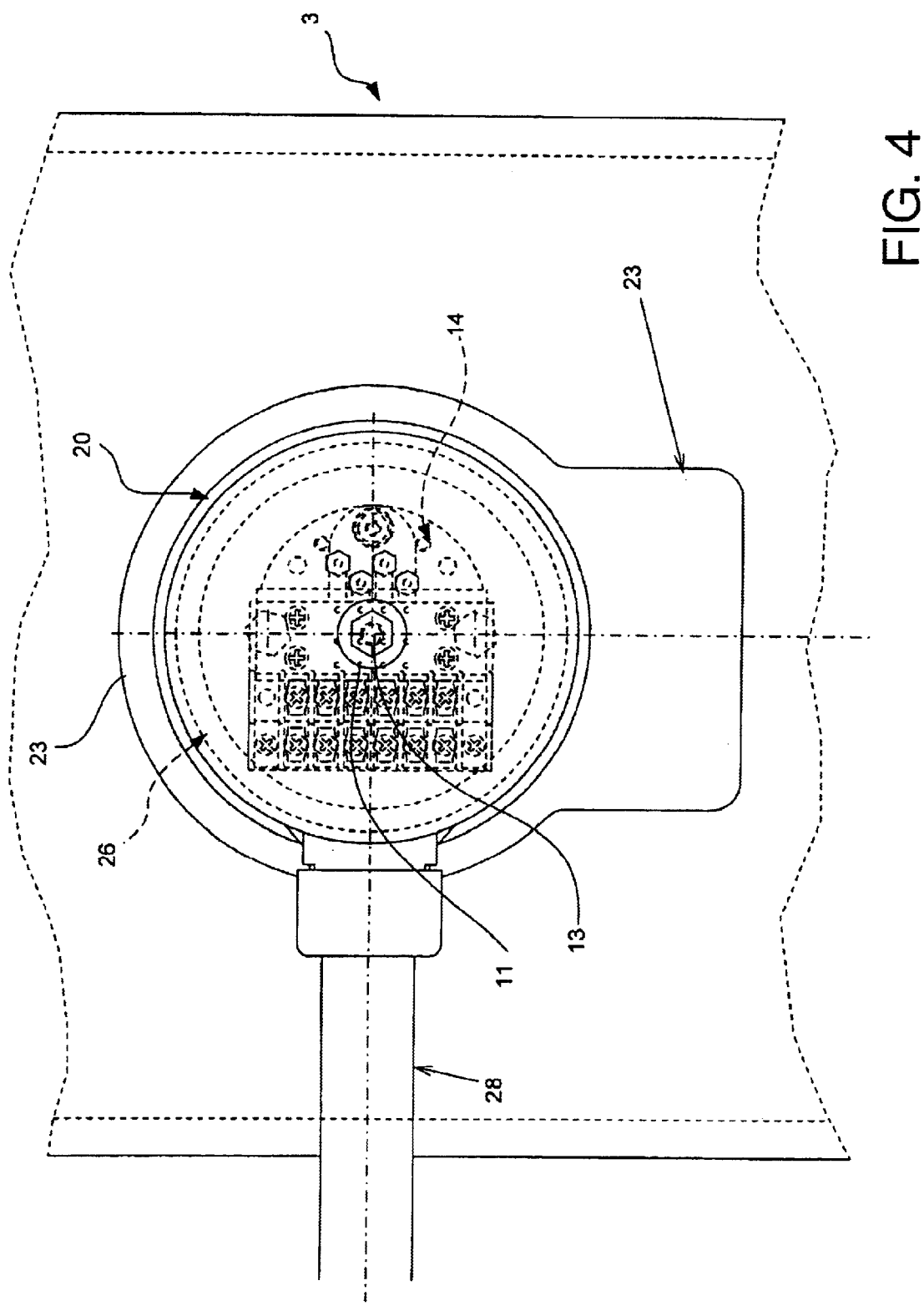
FIG. 4 is a bottom view of the gas density monitoring assembly of FIG. 2 connected to a tank, in accordance with one embodiment of the present invention.

FIGS. 3 and 4 illustrate further details of density monitoring apparatus 10 of FIG. 2. FIG. 3 is a cross-sectional view of density monitoring apparatus 10 of FIG. 2. Gas density monitoring apparatus 10 comprises a density monitor device 14 that measures gas pressure of the tank and/or tank temperature. Density monitor device 14 is coupled to tank 3 and is in fluidic communication with tank 3 by way of quick disconnect valve 18.

Density monitor device 14 is housed within a monitor device cover 12. In the present embodiment, monitor device cover 12 comprises aluminum; however, in other embodiments cover 12 may comprise steel, plastic, fiberglass, and the like. Monitor device cover 12 is lined with an insulative liner 26. In the present embodiment, liner 26 comprises ¼ inch closed cell polyethylene foam insulation; however, in other embodiments liner 26 may comprise neoprene, polyurethane, styrofoam, or the like.

A substantially U-shaped (cross-section) gasket 20 is disposed between monitor device cover 12 and tank 3. In the present embodiment, U-shaped gasket 20 is attached to cover 12 with standard super glue; however, any suitable adhesive is contemplated. Monitor device cover 12 is attached to density monitor device 14 by way of bolt 15 and washer 11; however, cover 12 may be attached with threads, a cotter pin, or the like.

Quick disconnect valve 18 is coupled to tank 3 proximate to tank boss 23. In the present embodiment, quick disconnect valve 18 is coupled to tank 3 via mounting plate 60. Mounting plate 60 is coupled to tank 3 with bolts 61. Bolts 61 secure mounting plate 60 and quick disconnect valve 18 to tank 3. In other embodiments, quick disconnect valve 18 may be welded to tank 3 or otherwise securely attached.

To provide a seal, a sealing system is applied between mounting plate 61 and tank 3. In the present embodiment, a double o-ring is located between plate 61 and tank 3. Mounting plate 61 is coupled to tank 3 via mounting bolts. The double o-ring seals provide a reliable robust sealing system, even if mounting bolts. are not fully tightened. In other embodiments, the sealing system may be a single o-ring, a flat gasket, a metal to metal seal or the like.

Quick disconnect valve 18 is coupled to mounting plate 50. Quick disconnect valve 18 is adapted to receive quick disconnect fitting 24. Quick disconnect valve 18 is open when quick disconnect fitting 24 is coupled to it and close when quick disconnect fitting 24 is not coupled to it. In this manner, quick disconnect valve 18 is always in the proper state and is therefore, fail-safe. That is, valve 18 automatically closes upon removal of quick disconnect fitting 24 and automatically opens upon coupling of quick disconnect fitting 24. This provides a fail-safe connection to tank 3, as well as provides little gas loss upon removal of quick disconnect fitting 24.

Figure 9:
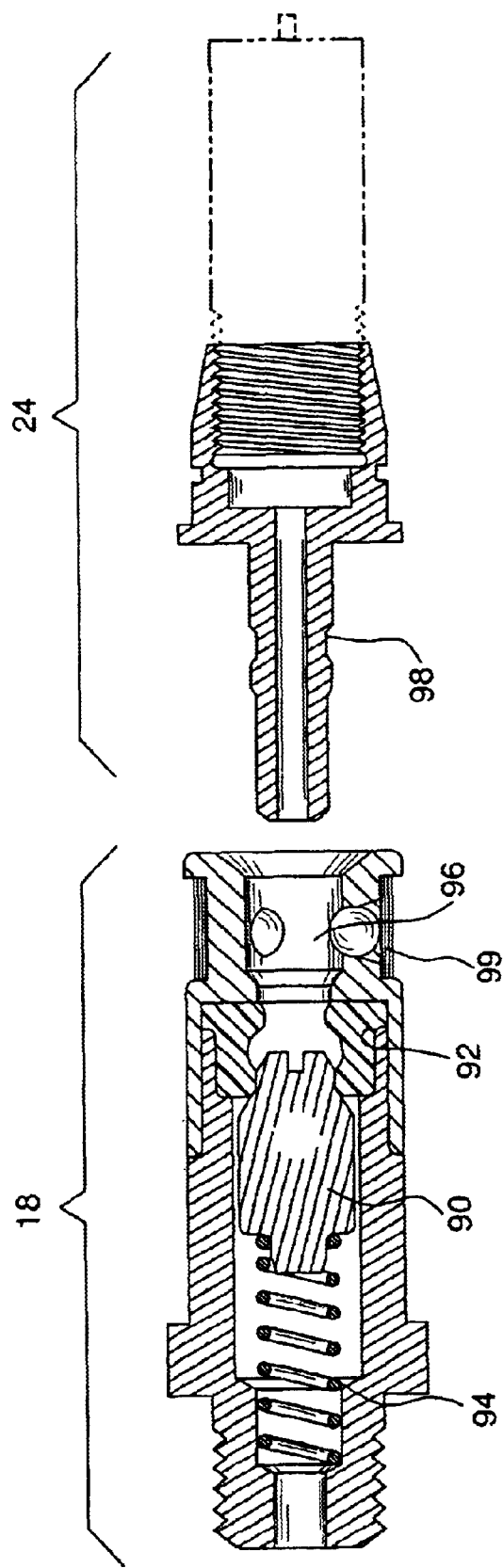
FIG. 9 is a sectional view of a quick disconnect valve and fitting, in accordance with one embodiment of the present invention.

Quick disconnect valves are known in the art and a variety of quick disconnect valves may be used in the present invention. For example, in the present embodiment as illustrated in. FIG. 9, quick disconnect valve 18 includes a valve body 90, a valve seat 92, and a spring 94. Spring 94 biases valve body 90 into valve seat 92, thereby closing quick disconnect valve 18. When quick disconnect fitting 24 is engaged into quick disconnect valve 18, valve body 90 is biased away from valve seat 92 and spring 94 is compressed, thereby opening quick disconnect valve 18. Quick disconnect valve 18 includes circumferentially spaced balls 96 for maintaining valve 18 in the open position. Balls 96 are biased towards the axial center of valve 18 by a spring 99. Quick disconnect fitting 24 includes a groove 98 for receiving circumferentially spaced balls 96. When quick disconnect fitting 24 is engaged into quick disconnect valve 18, circumferentially spaced balls 96 are biased into groove 98, thereby securing quick disconnect fitting 24 into quick disconnect valve 18. Such a quick disconnect fitting is described in more detail in U.S. Pat. No. 5,544,858, which is hereby incorporated by reference in its entirety.

Figure 10:
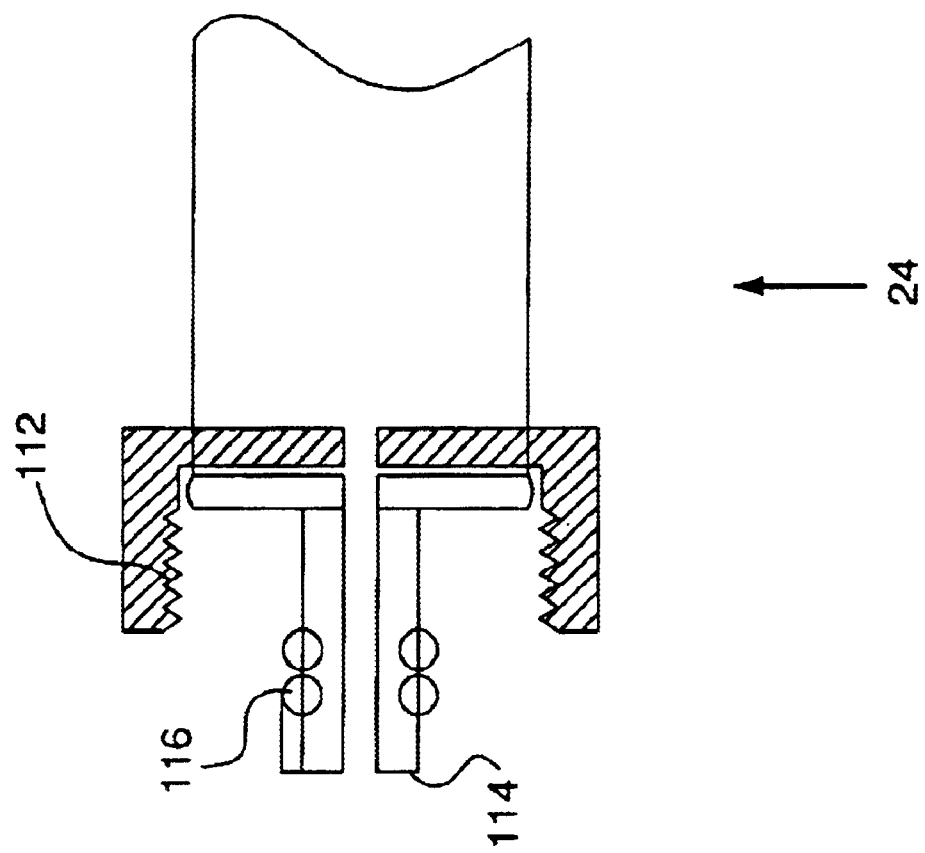
FIG. 10 is a sectional view of another quick disconnect valve and fitting, in accordance with another embodiment of the present invention.
Figure 10:
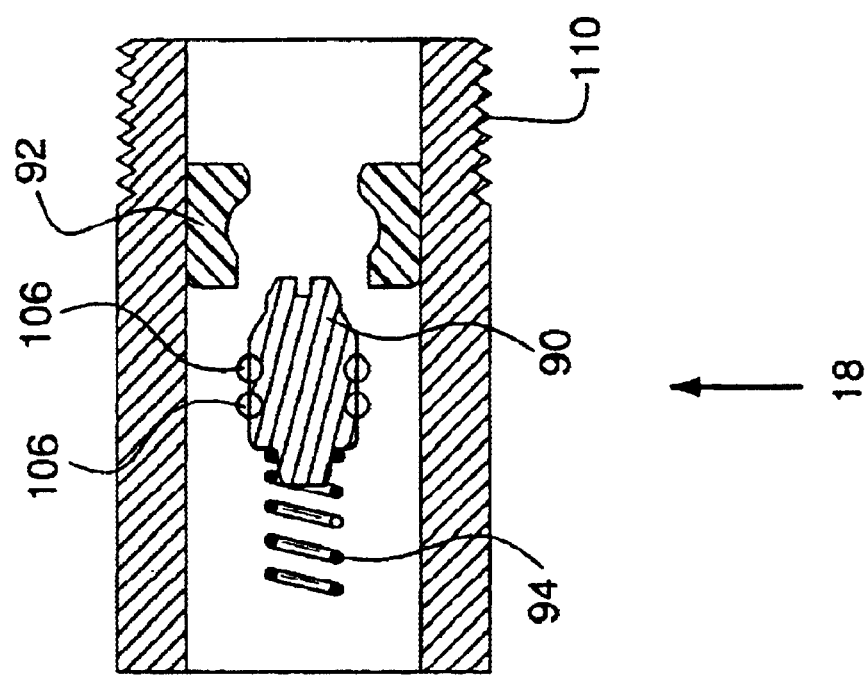

In another embodiment as illustrated in FIG. 10, quick disconnect valve 18 includes a valve body 100, a valve seat 102, and a spring 104. Spring 104 biases valve body 100 into valve seat 102, thereby closing quick disconnect valve 18. When quick disconnect fitting 24 is engaged into quick disconnect valve 18, valve body 100 is biased away from valve seat 102 by face 114 of quick disconnect fitting 24 and spring 104 is compressed, thereby opening quick disconnect valve 18. To provide a good seal between valve body 100 and valve seat 102, valve body 100 includes a double o-ring 106. To secure quick disconnect valve 18 to quick disconnect fitting 24, quick disconnect valve 18 includes male threads 110 and quick disconnect fitting includes complementary female threads 112.

In the present embodiment, face 114 is located a predetermined axial distance from female threads 112 such that threads 110, 112 form a seal before valve body 100 is un-seated from valve seat 102. In this manner, only a small amount of fluid escapes from tank 3 during coupling and uncoupling of the quick disconnect fitting. Further, the double o-ring 106 provides a seal between valve body 100 and valve seat 102 even when male threads 110 are not completely engaged in female threads 112.

In other embodiments, however, valve body 100 may unseat from valve seat 102 before threads 110, 112 form a seal. U.S. Pat. No. 4,889,368, which is hereby incorporated by reference in its entirety, describes a similar system.

In the present embodiment, quick disconnect fitting 24 further comprises a double o-ring 116 such that an o-ring seal is formed when the quick disconnect fitting 24 is coupled to the quick disconnect valve 18. The double o-ring seal provides a reliable robust sealing system; however, other sealing systems may be used. Preferably, quick disconnect valve 18 is selected with a flow capacity that allows tank 3 to be filled in a reasonable amount of time. One such quick disconnect valve 18 is model number 2541-925-V available from O. Malmquist AB, Box 53, 34221 Alvista, Sweden.

Quick disconnect valve 18 and quick disconnect fitting 24 may be any of a variety of suitable coupling systems. For example, quick disconnect valve 18 may include a vibration absorbing member as described in U.S. Pat. No. 5,248,168, which is hereby incorporated by reference in its entirety. Also, quick disconnect fitting 24 may include a second valve body and valve seat as described in U.S. Pat. No. 4,485,845 and U.S. Pat. No. 4,871,195, which are both hereby incorporated by reference in their entirety. Further, quick disconnect fitting 24 and quick disconnect valve 18 may be secured together in various ways. For example, a locking pin and aligned pin holes may be used, such as described in U.S. Pat. No. 4,871,195, and which is hereby incorporated by reference in its entirety.

Quick disconnect valve 18 extends beyond the outside surface of tank 3 a predetermined distance to cooperate with quick disconnect fitting 24, such that when quick disconnect fitting 24 is coupled to quick disconnect valve 18, monitor device cover 12 is coupled to the outside surface of tank 3.

Quick disconnect fitting 24 is coupled to density monitor device 14 such that fluidic pressure may pass through quick disconnect fitting 24 to monitor device 14. That is, quick disconnect fitting 24 is coupled to monitor device 14 such that interior of quick disconnect fitting 24 is in fluidic communication with the interior of monitor device 14. Quick disconnect fitting 24 is adapted to be coupled to the quick disconnect valve 18 of tank 3, as described above.

With a quick disconnect fitting, the monitor device may be quickly coupled and un-coupled to the tank. The quick disconnect valve closes when there is no corresponding quick disconnect fitting coupled to it. In this manner, calibrations can be easily performed by simply removing density monitor 14 from tank 3 and performing a calibration with a predetermined gas pressure (as a proxy for density) and the output of density monitor device 14 compared to a benchmark value. After calibration, density monitor 14 is re-coupled to the tank via the quick disconnect fitting 24. Because the valve automatically opens and close at the appropriate times, little gas is lost during the coupling and un-coupling.

Monitor device cover 12 is coupled to monitor device 14 and extends a predetermined distance beyond density monitor device 14, such that, when quick disconnect fitting 24 is coupled to quick disconnect valve 18, monitor device cover 12 is coupled to tank 3. In one embodiment, cover 12 and monitor device 14 are sized such that cover 12 does not seat against tank boss 23 unless male threads 110 are fully engaged in female threads 112. Thus, this configuration may provide a fully open quick disconnect valve 18 when cover 12 is seated against tank boss 23 (e.g., when monitor device 14 is in use).

Monitor device cover 12 is disposed over monitor device 14 and against the outside wall of tank 3 to maintain monitor device 14 at approximately the temperature of tank 3, theoretically providing a more accurate estimation of gas density.

Figure 8:
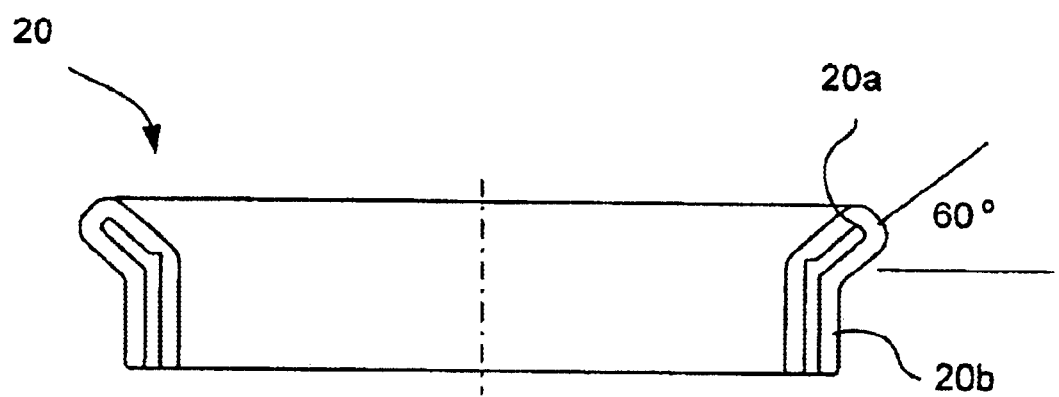
FIG. 8 illustrates a cut-away side view of a gasket employed in a gas density monitoring assembly, in accordance with one embodiment of the present invention.

In the present embodiment, monitor device cover 12 is coupled to the outside wall of tank 3 via a gasket 20. U-shaped gasket 20 is attached to a rim of cover 14. FIG. 8 illustrates a cross-sectional side view of gasket 20. As shown, gasket 20 comprises an upstanding portion 20b and an angled portion 20a. Angled portion 20a forms an angle of approximately 60 degrees. In the present embodiment, the gasket is formed of a low temperature vinyl; however, other gasket materials are contemplated.

As a result of the combination of the material (e.g., soft vinyl) and the selected angle (e.g., angle of 20a), the gasket forms a stable, high friction base and seal for monitor device cover 12 as it is pressed against the raised boss 23 formed into tank 3. Gasket 20 provides protection against ingress of liquid into the interior of monitor device cover 12. Gasket 20 also provides additional mechanical stability to density monitoring apparatus 10 when quick disconnect fitting 24 is coupled to quick disconnect valve 18.

A conduit 28 is coupled to monitor device cover 12 and provides a passage for electrical wires 17 to provide electrical signals from density monitor device 14 back to an electrical control panel (not shown). Electrical wires 17 connect to density monitor device 14 by way of terminal block 14b (see FIGS. 5–7).

Weep holes 31 may be provided in monitor device cover 12. Weep holes 31 provide a means of egress for any condensation or moisture in monitor device cover 12.

Figure 5:
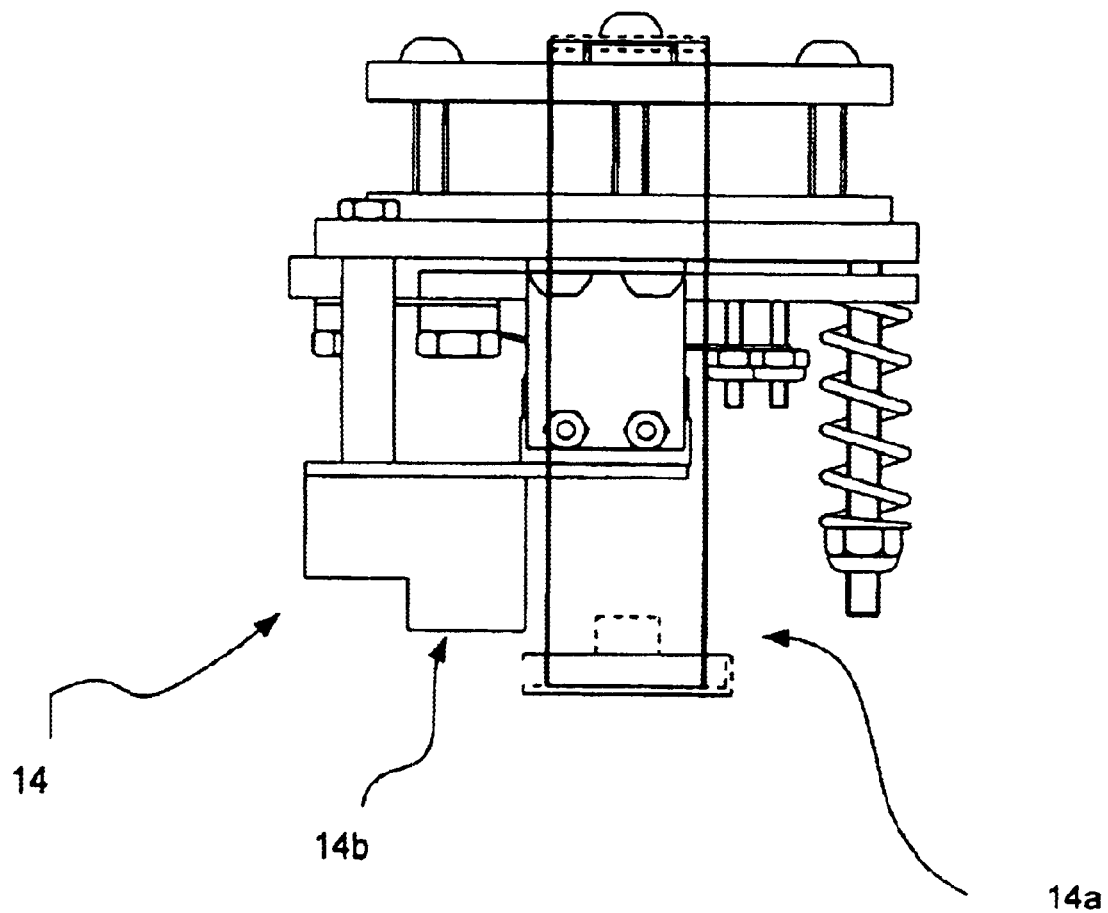
FIGS. 5–7 illustrate a side, top, and front plan view, respectively, of a gas density monitor device employed in one embodiment of the present invention.
Figure 7:
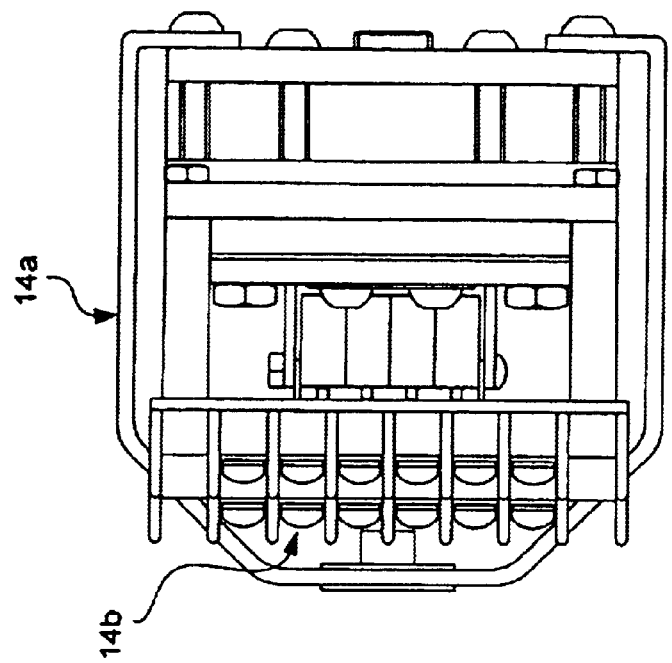
Figure 6:
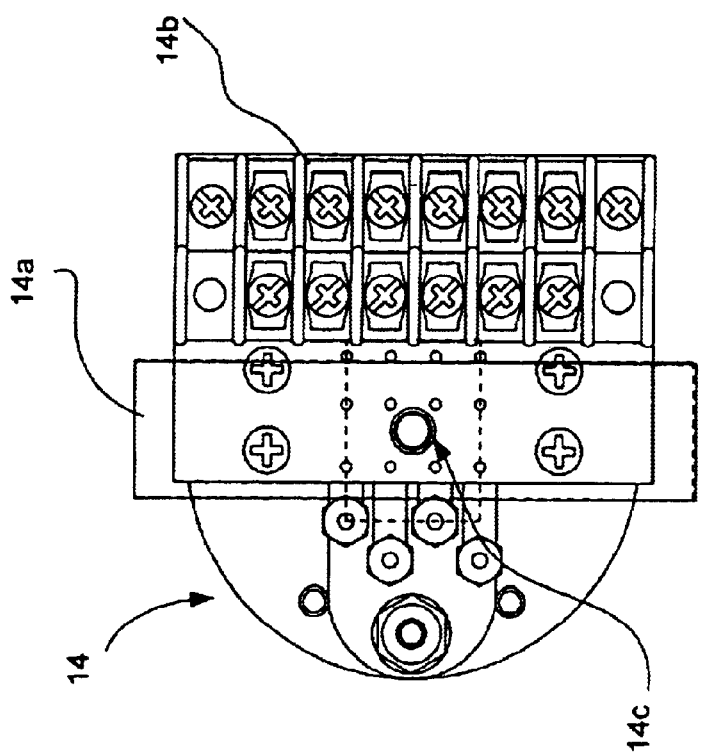

Density monitor device 14 is best shown in FIGS. 5–7. Density monitor device 14 comprises a terminal block 14b that comprises a set of terminals to which signal leads (e.g., leads 17 shown in FIG. 3) can be attached to carry electrical information to a control panel (not shown). Density monitor device 14 may output, for example, temperature and pressure information (e.g., as analog signals such as 4–20 mA signals) from which the gas density can be calculated. Alternatively, the density monitor device 14 may output discrete signals representative of discrete density levels (e.g., discrete switch closure signals indicative of discrete density levels corresponding to predefined setpoints). A rigid support member 14a wraps around density monitor device 14 so that monitor device cover 12 can be attached to the density monitor device and thereby pressed firmly against tank 3. FIG. 6 best illustrates a screw hole 14c whereby bolt 13 attaches monitor device cover 12 to support member 14a.

As noted, $SF_6$ gas density can computed by measuring gas pressure and tank temperature. The temperature input may be a resistive temperature device (RTD) mounted within monitor device cover 12. Insulative liner 26 insures that the temperature within cover 12 remains a good proxy for tank temperature. Pressure signals may originate in a strain gage transducer mounted on a circuit board within density monitor device 14.

Alternatively, the gas density can be determined by using a mechanical device that directly converts temperature and pressure to a density level. Such devices employ a series of switches representative of a discrete density level. For example, when the density level is at a satisfactory level, the gas pressure causes a first set of electro-mechanical contacts to close. As the gas pressure, changes to a second discrete level a second set of contact would close indicative of the second level and so on. Alarms can be set for each particular contact set.

As can be seen, the present invention provides a simple, self-supporting, and economical apparatus for mounting a density monitor to a tank. Traditional threaded gas piping is not required, thereby reducing a major source of gas leaks. The apparatus allows easy access to the density monitor for maintenance and calibration and provides a fail-safe valve for connection between the tank and the density monitor.

It is noted that the foregoing illustrative embodiments have been provided merely for the purpose of explanation and are in no way to be construed as limiting of the present invention. While the invention has been described with reference to illustrative embodiments, it is understood that the words which have been used herein are words of description and illustration, rather than words of limitation. Further, although the invention has been described herein with reference to particular structure, methods, materials, and embodiments, the invention is not intended to be limited to the particulars disclosed herein; rather, the invention extends to all structures, methods and uses that are within the scope of the appended claims.

What is claimed is:

1. An assembly for monitoring the fluidic contents of a tank having a quick disconnect valve, the assembly comprising:
   a monitor device having an interior;
   a monitor device cover disposed over the monitor device, the monitor device cover comprising a rim; and
   a quick disconnect fitting having a fitting interior, the quick disconnect fitting coupled to the monitor device such that the fitting interior is in fluidic communication with the interior of the monitor device, wherein the rim is disposed a predetermined distance from the quick disconnect fitting, such that when the quick disconnect fitting is coupled to the quick disconnect valve, the rim is coupled to an outside wall of the tank.

2. The assembly as recited in claim 1 wherein the quick disconnect fitting comprises an o-ring, whereby an o-ring seal is formed when the quick disconnect fitting is coupled to the quick disconnect valve.

3. The assembly as recited in claim 1 further comprising an insulator attached to an inside surface of the monitor device cover to maintain a temperature within the cover in relation to a temperature of the tank.

4. The assembly as recited in claim 1 comprising a gasket disposed between the monitor device cover and the tank.

5. The assembly as recited in claim 1 wherein the monitor device comprises a gas density monitor.

6. The assembly as recited in claim 5 wherein the gas density monitor comprises one of a pressure monitor and temperature monitor.

7. A system for monitoring the fluidic contents of a tank, comprising:
   a quick disconnect valve attached-to the outer surface of the tank;
   a quick disconnect fitting coupled to the quick disconnect valve; and a density monitor device having an interior, the density monitor device coupled to the quick disconnect fitting such that interior of the tank is in fluidic communication with the interior of the monitor device.

8. The system as recited in claim 7 further comprising a monitor device cover having a top, side walls, and a rimmed open bottom, the cover being disposed over the density monitor device.

9. The system as recited in claim 8 wherein the rim of the monitor device cover is disposed a predetermined distance from the quick disconnect fitting, such that when the quick disconnect fitting is coupled to the quick disconnect valve of the tank, the rim is coupled to an outside wall of the tank.

10. The system as recited in claim 7 wherein the quick disconnect fitting comprises an o-ring, whereby an o-ring seal is formed when the quick disconnect fitting is coupled to the quick disconnect valve.

11. The system as recited in claim 7 further comprising an insulator attached to an inside surface of the monitor device cover to maintain a temperature within the cover in relation to a temperature of the tank.

12. The system as recited in claim 7 wherein the monitor device comprises a gas density monitor.

13. The system as recited in claim 12 wherein the gas density monitor comprises one of a pressure monitor and temperature monitor.

14. An assembly for monitoring the fluidic contents of a tank having a quick disconnect valve, the quick disconnect valve comprising a valve seat, a valve body, and a spring biasing the valve body towards the valve seat, the assembly comprising:

a monitor device having an interior;

a monitor device cover disposed over the monitor device, the monitor device cover comprising a rim; and a quick disconnect fitting being substantially cylindrical, having a face at one end of the cylinder, and having an interior, the quick disconnect fitting coupled to the monitor device such that interior of the quick disconnect fitting is in fluidic communication with the interior of the monitor device, and the quick disconnect fitting coupled to the quick disconnect valve such that the face of the cylinder biases the valve body of the quick disconnect valve away from the valve seat, thereby allowing fluidic communication between the tank and the monitor device, wherein the rim is disposed a predetermined distance from the quick disconnect fitting, such that when the quick disconnect fitting is coupled to the quick disconnect valve, the rim is coupled to an outside wall of the tank.

15. The assembly as recited in claim 14 wherein the quick disconnect fitting comprises an o-ring, whereby an o-ring seal is formed when the quick disconnect fitting is coupled to the quick disconnect valve.

16. The assembly as recited in claim 14 wherein the valve body comprises an o-ring, whereby an o-ring seal is formed between the valve body and the valve seat when the quick disconnect fitting is not coupled to the quick disconnect valve.

17. The assembly as recited in claim 14 wherein the quick disconnect valve comprises a male thread and the quick disconnect fitting comprises a complementary female thread.

18. The assembly as recited in claim 17 wherein the female thread of the quick disconnect fitting is spaced a predetermined axial distance from the face such that the valve body remains seated in the valve seat until a predetermined number of threads are engaged.

19. The assembly as recited in claim 14 wherein the monitor device comprises a gas density monitor.

20. The assembly as recited in claim 19 wherein the gas density monitor comprises one of a pressure monitor and temperature monitor.

21. An assembly for monitoring the fluidic contents of a tank having a quick disconnect valve, the quick disconnect valve comprising a valve seat, a valve body, and a spring biasing the valve body towards the valve seat, the assembly comprising:

a monitor device having an interior;

a quick disconnect fitting being substantially cylindrical, having a face at one end of the cylinder, and having an interior, the quick disconnect fitting coupled to the monitor device such that interior of the quick disconnect fitting is in fluidic communication with the interior of the monitor device, and the quick disconnect fitting coupled to the quick disconnect valve such that the face of the cylinder biases the valve body of the quick disconnect valve away from the valve seat, thereby allowing fluidic communication between the tank and the monitor device, wherein the valve body comprises an o-ring, whereby an o-ring seal is formed between the valve body and the valve seat when the quick disconnect fitting is not coupled to the quick disconnect valve.

22. The assembly as recited in claim 21 further comprising a monitor device cover disposed over the monitor device.

23. The assembly as recited in claim 21 wherein the quick disconnect fitting comprises an o-ring, whereby an o-ring seal is formed when the quick disconnect fitting is coupled to the quick disconnect valve.

24. The assembly as recited in claim 21 wherein the valve body comprises an o-ring, whereby an o-ring seal is formed between the valve body and the valve seat when the quick disconnect fitting is not coupled to the quick disconnect valve.

25. The assembly as recited in claim 21 wherein the quick disconnect valve comprises a male thread and the quick disconnect fitting comprises a complementary female thread.

26. The assembly as recited in claim 21 wherein the female thread of the quick disconnect fitting is spaced a predetermined axial distance from the face such that the valve body remains seated in the valve seat until a predetermined number of threads are engaged.

27. The assembly as recited in claim 21 wherein the monitor device cover includes a rim, the rim disposed a predetermined distance from the quick disconnect fitting, such that when the quick disconnect fitting is coupled to the quick disconnect valve, the rim is coupled to an outside wall of the tank.

* * * * *